United States Patent [19]

Wichman

[11] Patent Number: 4,462,396
[45] Date of Patent: Jul. 31, 1984

[54] SURGICAL DRAPE
[75] Inventor: Cynthia A. Wichman, St. Charles, Ill.
[73] Assignee: The Kendall Company, Boston, Mass.
[21] Appl. No.: 461,349
[22] Filed: Jan. 27, 1983
[51] Int. Cl.$^3$ ............................................. A61B 19/06
[52] U.S. Cl. ................................................ 128/132 D
[58] Field of Search ................... 128/132 D, 132, 292, 128/286, 287, ; 2/49 R, 49 A

[56] References Cited

U.S. PATENT DOCUMENTS

| | | | |
|---|---|---|---|
| 3,791,382 | 2/1974 | Collins | 128/132 D |
| 4,089,331 | 5/1978 | Hartigan et al. | 128/132 D |
| 4,169,472 | 10/1979 | Morris | 128/132 D |
| 4,275,720 | 6/1981 | Wichman | 128/132 D |
| 4,414,968 | 11/1983 | Amin | 128/132 D |

Primary Examiner—Stephen C. Pellegrino
Attorney, Agent, or Firm—Powell L. Sprunger

[57] ABSTRACT

A surgical drape comprising, a main sheet of flexible material having an inner surface for facing a patient after placement of the drape, an outer surface for facing away from the patient after placement of the drape, and a fenestration. The drape has a pocket comprising a secondary sheet of flexible material having a pair of end edges, a pair of side edges connecting the end edges, a first surface, and an opposing second surface. The secondary sheet has a first fold line extending between the end edges at a location between the side edges and defining a pair of first and second panels extending between the first fold line and the side edges. The first surface of the first and second panels face each other in the folded sheet. The first and second panels have second and third fold lines defining a pair of opposed first and second flaps and a central portion extending between the flaps. The second and third fold lines extend from the juncture of the end and side edges to the first fold line at a location spaced from the end edges. The flaps are folded against the first panel. The central portion defines a cavity communicating with an opening defined by the side edges. The flaps are secured to the central portion, and the pocket is secured to the main sheet with the opening facing toward the expected path of fluid run-off from the fenestration.

10 Claims, 6 Drawing Figures

SURGICAL DRAPE

BACKGROUND OF THE INVENTION

The present invention relates to surgical drapes.

During certain medical procedures, such as gynecology, cystoscopy, or hemorrhoidectomy, where the patient is in a lithotomy position, fluid run-off, such as saline solution or blood, can be a problem. Blood loss, especially if excessive, should be measured. In cystoscopy procedures, saline solution is used to flush the surgical site, and the tissue should be collected for laboratory analysis. The saline solution should be drained away from the surgical site, and should be kept contained so that it does not go onto the floor. Prior drapes have not proved adequate for collecting the run-off fluid, and the tissue specimens.

SUMMARY OF THE INVENTION

A principal feature of the present invention is the provision of an improved surgical drape of simplified construction.

The drape of the present invention comprises, a main sheet of flexible material having an inner surface for facing a patient after placement of the drape, an outer surface for facing away from the patient after placement of the drape, and a fenestration. The drape has a pocket comprising a secondary sheet of flexible material having a pair of end edges, a pair of side edges connecting the end edges, a first surface, and an opposing second surface. The secondary sheet has a first fold line extending between the end edges at a location between the side edges and defining a pair of first and second panels extending between the first fold line and the side edges. The first surface of the first and second panels face each other in the folded sheet. The first and second panels have second and third fold lines defining a pair of opposed first and second flaps and a central portion extending between the flaps. The second and third fold lines extend from the juncture of the end and side edges to the first fold line at a location spaced from the end edges. The flaps are folded against the first panel. The central portion defines a cavity communicating with an opening defined by the side edges. The drape has means for securing the flaps to the central portion, and means for securing the pocket to the main sheet with the opening facing toward the expected path of fluid run-off from the fenestration.

A feature of the present invention is that the pocket is constructed in a simplified manner, and is relatively inexpensive to fabricate.

Another feature of the present invention is that the pocket construction is sturdy without the need of additional reinforcement, and does not collapse when collecting run-off fluids.

A further feature of the invention is that the pocket is part of the drape so that no additional components are required in order to simplify the draping procedure.

Yet another feature of the invention is that the drape eliminates the need for a fully equipped cystoscopy table.

Still another feature of the invention is that the cleanup after the surgical procedure has been completed is easier because drawers on a cystoscopy table need not be used and cleaned.

Yet another feature of the pocket is that the pocket may have a drain opening and drain tube in order to drain the fluids from the pocket.

Still another feature of the invention is that the drape may have a screen over the drain opening to collect tissue specimens.

Further features will become more fully apparent in the following description of the embodiments of this invention and from the appended claims.

DESCRIPTION OF THE PREFERRED EMBODIMENTS

Figure 1:
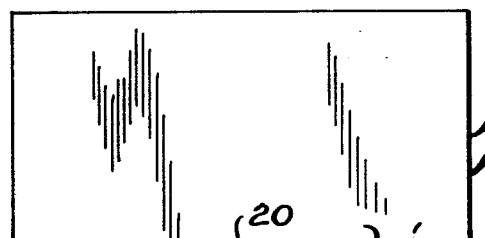
FIG. 1 is a plan view of a surgical drape of the present invention.

Referring now to FIG. 1, there is shown a surgical drape generally designated 10 having a main sheet 12 and a pocket 14 secured to the main sheet 12. The main sheet 12 is constructed of flexible material, such as a nonwoven material. The main sheet 12 has an inner surface 16 for facing the patient after placement of the drape, an outer surface 18 for facing away from the patient after placement of the drape, and a fenestration 20 extending through the main sheet 12.

Figure 2:
FIGS. 2-4 are perspective views illustrating folding of a sheet to form a pocket for the drape of FIG. 1.

Referring now to FIG. 2, the pocket 14 comprises a generally rectangular secondary sheet 22 of suitable flexible material, such as a nonwoven material. The secondary sheet 22 has a pair of generally aligned end edges 24a and 24b, a pair of generally aligned side edges 26a and 26b connecting the end edges 24a and b, a first surface 28, and an opposing second surface 30. As shown, the secondary sheet 22 has a first fold line 32 extending between the end edges 24a and b at a location generally centrally between the side edges 26a and b, and defining a pair of first and second panels 34 and 36, respectively, which extend between the first fold line 32 and the side edges 26a and b. The first surface 28 of the first and second panels 34 and 36 face each other in the folded sheet 22, and the side edges 26a and b of the first and second panels 34 and 36 are located adjacent each other in the folded sheet 22.

Figure 3:
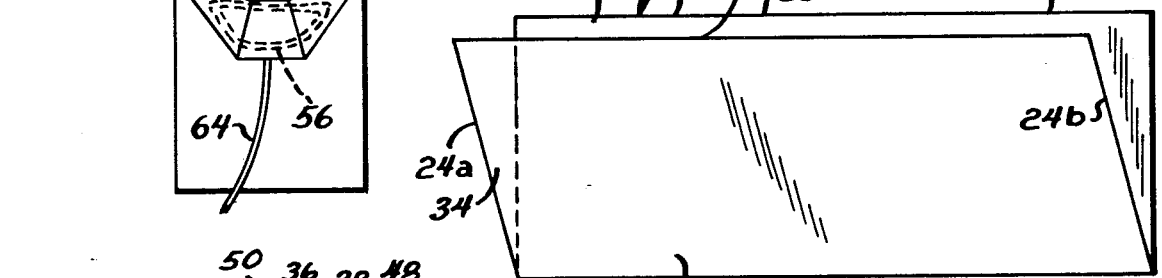

With reference to FIG. 3, the first and second panels 34 and 36 have second and third fold lines 38 and 40, respectively, defining a pair of opposed first and second flaps 42 and 44, respectively, and a central portion 46 extending between the flaps 42 and 44. The second and third fold lines 38 and 40 extend from the juncture of the end edges 24a and b and the side edges 26a and b to the first fold line 32 at a location spaced from the end edges 24a and b. In a preferred form, as shown, the end edges 24a and b of the first and second flaps 42 and 44 are located adjacent the side edges 26a and b of the central portion 46. This construction may be accomplished while making the second and third fold lines 38 and 40 generally at a 45° angle to the first fold line 32. As shown, the first and second flaps 42 and 44 are folded against the first panel 34. In this form, the central portion 46 of the drape 10 defines a cavity 48 which communicates with an opening 50 defined by the side edges 26a and b. The two panels of the flaps 42 and 44 may be secured together by suitable adhesive 52, and the first and second flaps 42 and 44 may be secured to the central portion 46 by adhesive 54. Also, with reference to FIG. 1, the formed pocket 14 may be secured to the outer surface 18 of the main sheet 12 by suitable adhesive 56 in a configuration with the opening 50 facing toward the expected path of fluid run-off from the fenestration 20. In a preferred form, the second panel 36 of the pocket 14 faces the outer surface 18 of the main sheet 12 when the pocket 14 is secured to the main sheet 12.

Figure 4:
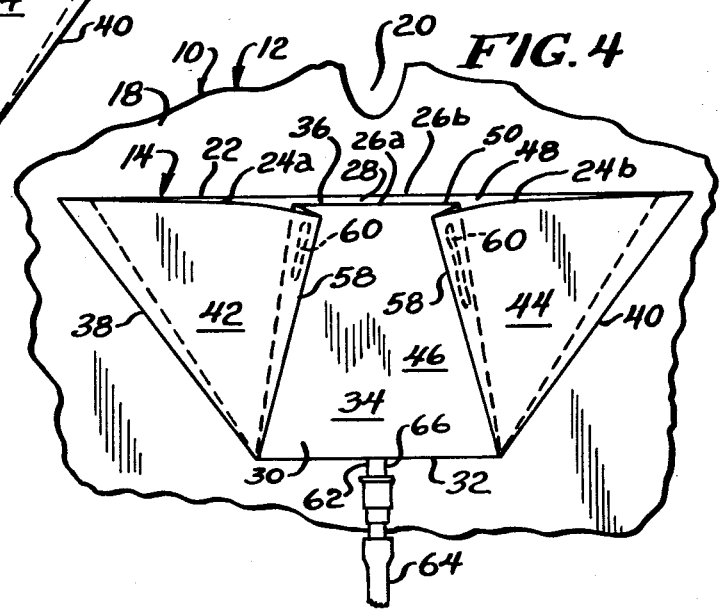

With reference to FIG. 4, the first panel 34 of the pocket 14 may have one or more tucks 58 extending from the first fold line 32 to the side edge 26a of the first panel 34. In a preferred form, the pocket 14 has a pair of tucks 58 located adjacent the first fold line 32 of the first and second flaps 42 and 44. As shown, the tucks 58 may be secured together by suitable adhesive 60.

Figure 5:
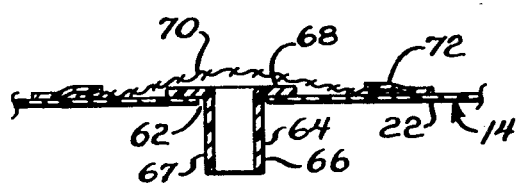
FIG. 5 is a fragmentary sectional view of a lower part of the pocket.

With reference to FIGS. 4 and 5, the pocket 14 has a lower drain opening 62 adjacent the first fold line 32 in the central portion 46. The drape 10 also has a drain tube 64 communicating with the drain opening 62, such that fluid may be drained from the cavity 48 to a kick bucket, a drain on the floor, or a receptacle to collect and measure the fluid. As shown, the drain tube 64 has a coupling 66 received in the drain opening 62, with the coupling 66 having a tubular portion 67, and an annular flange 68 secured to the pocket 14 around the opening 62. In the embodiment of FIG. 5, the pocket 14 has a screen 70 located over the drain opening 62 in order to collect tissue specimens that fall into the cavity 48 of the pocket 14. The screen 70 may be secured to the pocket 14 by a suitable gasket 72 which is attached to the pocket 14 by suitable means, such as by adhesive.

Figure 6:
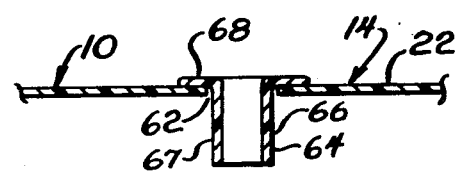
FIG. 6 is a fragmentary sectional view of another embodiment of a lower part of the pocket.

Another embodiment of the present invention is illustrated in FIG. 6, in which like reference numerals designate like parts. In this embodiment, the drape 10 is of identical construction with the drape of FIGS. 1-5, except that the screen may be omitted over the drain opening 62 for surgical procedures in which it is not necessary to collect tissue specimens.

The foregoing detailed description is given for clearness of understanding only, and no unnecessary limitations should be understood therefrom, as modifications will be obvious to those skilled in the art.

I claim:

1. A surgical drape, comprising:
   a main sheet of flexible material having an inner surface for facing a patient after placement of the drape, an outer surface for facing away from the patient after placement of the drape, and a fenestration;
   a pocket comprising a secondary sheet of flexible material having a pair of end edges, a pair of side edges connecting the end edges, a first surface, and an opposing second surface, said secondary sheet having a first fold line extending between said end edges at a location between said side edges and defining a pair of first and second panels extending between said first fold line and said side edges, with the first surface of said first and second panels facing each other in the folded sheet, said first and second panels having second and third fold lines defining a pair of opposed first and second flaps and a central portion extending between the flaps, said second and third fold lines extending from the juncture of the end and side edges to the first fold line at a location spaced from the end edges, said flaps being folded against the first panel, said central portion defining a cavity communicating with an opening defined by said side edges;
   means for securing the flaps to said central portion; and
   means for securing the pocket to the outer surface of the main sheet with said opening facing toward the expected path of fluid run-off from said fenestration.

2. The drape of claim 1 wherein the end edges of said flaps are located adjacent the side edges of said central portion.

3. The drape of claim 1 wherein said pocket includes a drain opening located adjacent said first fold line.

4. The drape of claim 3 including a screen located over said drain opening in said cavity.

5. The drape of claim 3 including a drainage tube communicating with said drain opening.

6. The drape of claim 1 including at least one tuck in said central portion extending from said first fold line to one of said side edges.

7. The drape of claim 6 including a pair of tucks in said first panel located adjacent the first fold line of said flaps.

8. The drape of claim 1 wherein the second panel faces the outer surface of the main sheet.

9. The drape of claim 1 in which the secondary sheet is generally rectangular, the end edges are generally aligned, the side edges are generally aligned, the first fold line is located generally centrally between the side edges, and the side edges of the first and second panels are located adjacent each other in the folded sheet.

10. A surgical drape, comprising:
    a main sheet of flexible material having an inner surface for facing a patient after placement of the drape, an outer surface for facing away from the patient after placement of the drape, and a fenestration;
    a pocket comprising a generally rectangular secondary sheet of flexible material having a pair of generally aligned end edges, a pair of generally aligned side edges connecting the end edges, a first surface, and an opposing second surface, said secondary sheet having a first fold line extending between said end edges at a location generally centrally between said side edges and defining a pair of first and second panels extending between said first fold line and said side edges, with the first surface of said first and second panels facing each other in the folded sheet, and with the side edges of the first and second panels being located adjacent each other in the folded sheet, said first and second panels having second and third fold lines defining a pair of opposed first and second flaps and a central portion extending between the flaps, said second and third fold lines extending from the juncture of the end and side edges to the first fold line at a location spaced from the end edges, said flaps being folded against the first panel, said central portion defining a cavity communicating with an opening defined by said side edges;
    means for securing the flaps to said central portion; and
    means for securing the pocket to the outer surface of the main sheet with said opening facing toward the expected path of fluid run-off from said fenestration.

* * * * *